US00PP21762P2

(12) United States Plant Patent
Stewart et al.

(10) Patent No.: US PP21,762 P2
(45) Date of Patent: Mar. 8, 2011

(54) STRAWBERRY PLANT NAMED 'DRISSTRAWFIFTEEN'

(50) Latin Name: *Fragaria×ananassa*
Varietal Denomination: DrisStrawFifteen

(75) Inventors: Philip J. Stewart, Watsonville, CA (US); Martin P. Madesko, Aptos, CA (US); JoAnne F. Coss, Pebble Beach, CA (US); Bruce D. Mowrey, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 12/592,083

(22) Filed: Nov. 19, 2009

(51) Int. Cl.
*A01H 5/00* (2006.01)

(52) U.S. Cl. ..... Plt./209

(58) Field of Classification Search ..... Plt./209

See application file for complete search history.

*Primary Examiner*—June Hwu
(74) *Attorney, Agent, or Firm*—Jondle & Associates, P.C.

(57) ABSTRACT

This invention relates to a new and distinct cultivar of strawberry plant named 'DrisStrawFifteen'. The new cultivar is primarily characterized by a flat globose plant habit, medium vigor, and medium-sized berries, is disclosed.

3 Drawing Sheets

Genus and species: *Fragaria×ananassa.*
Variety denomination: 'DrisStrawFifteen'.

BACKGROUND OF THE NEW PLANT

The present invention relates to a new and distinct strawberry cultivar designated 'DrisStrawFifteen' and botanically known as *Fragaria×ananassa*. This new strawberry cultivar was discovered in Monterey County, Calif. in June 2004 and originated from a cross between the proprietary female parent 'Driscoll Lanai' (U.S. Plant Pat. No. 15,145) and the proprietary male parent '38J181' (unpatented). The original seedling of the new cultivar was first asexually propagated at a nursery in Shasta County, Calif.

'DrisStrawFifteen' was subsequently asexually propagated at the McArthur Nursery in Shasta County, Calif. and underwent further testing in Monterey County, Calif. for six years. The present invention has been found to retain its distinctive characteristics through successive asexual propagations via stolons and tissue culture.

DESCRIPTION OF THE PHOTOGRAPHS

The accompanying color photographs show typical specimens of the new cultivar at various stages of development as nearly true as it is possible to make in color reproductions. The photographs were taken from 9½-month-old plants.

DESCRIPTION OF THE NEW CULTIVAR

Figure 1:
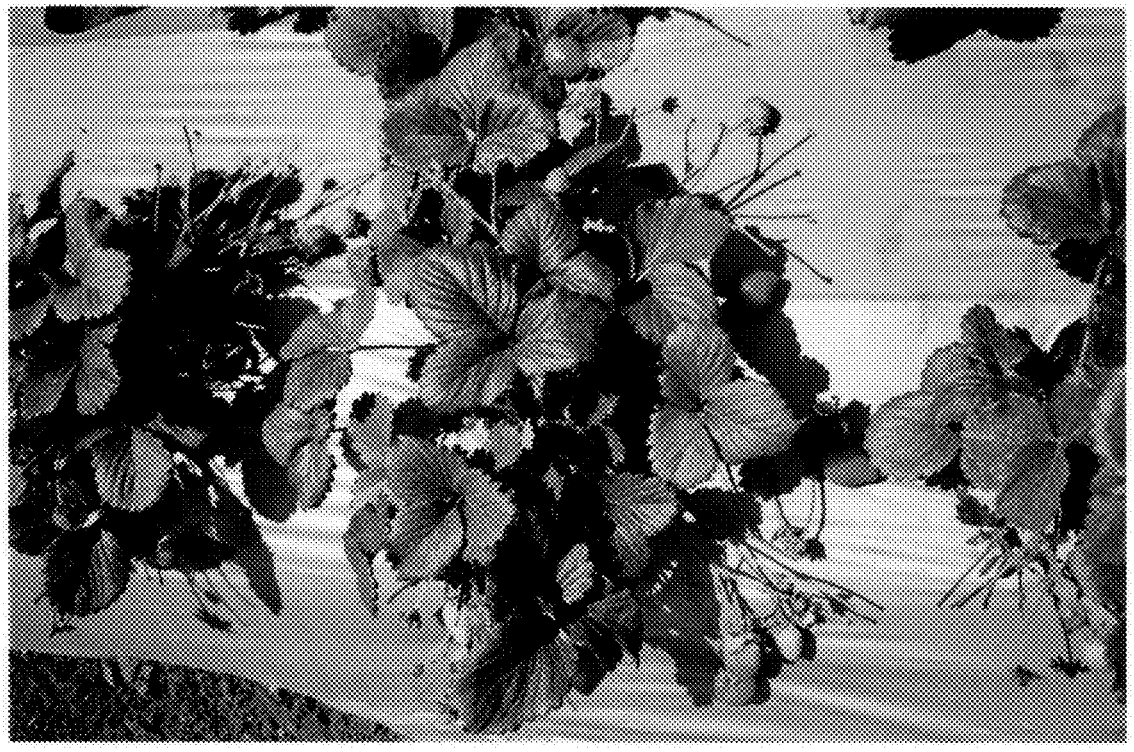
FIG. 1 shows overall plant habit including fruit at various stages of development.
Figure 2:
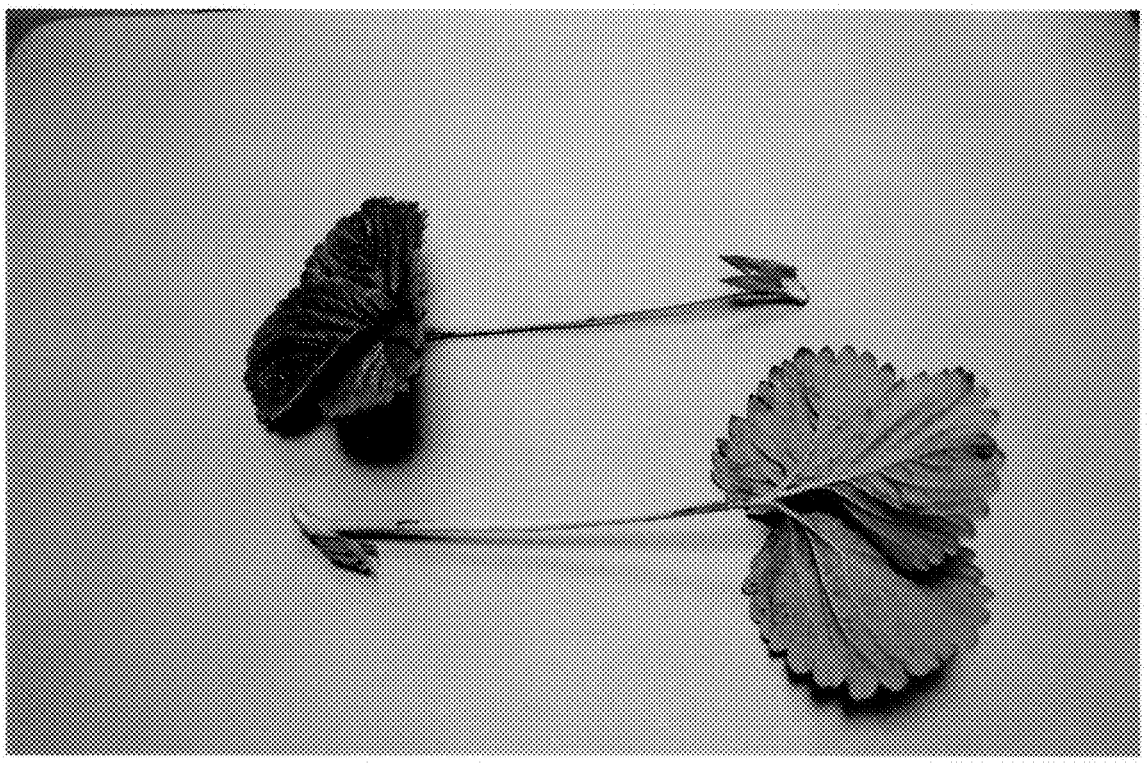
FIG. 2 shows leaves of the plant with three leaflets.
Figure 3:
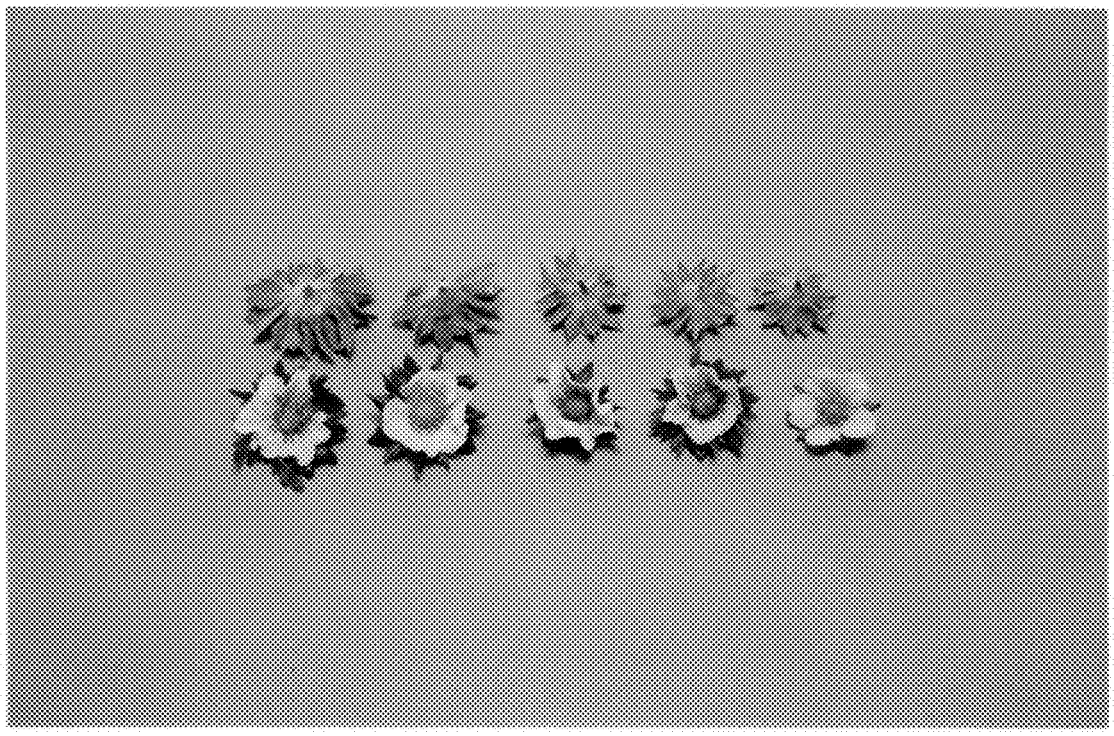
FIG. 3 shows both the upper side and underside of several of the flowers.
Figure 4:
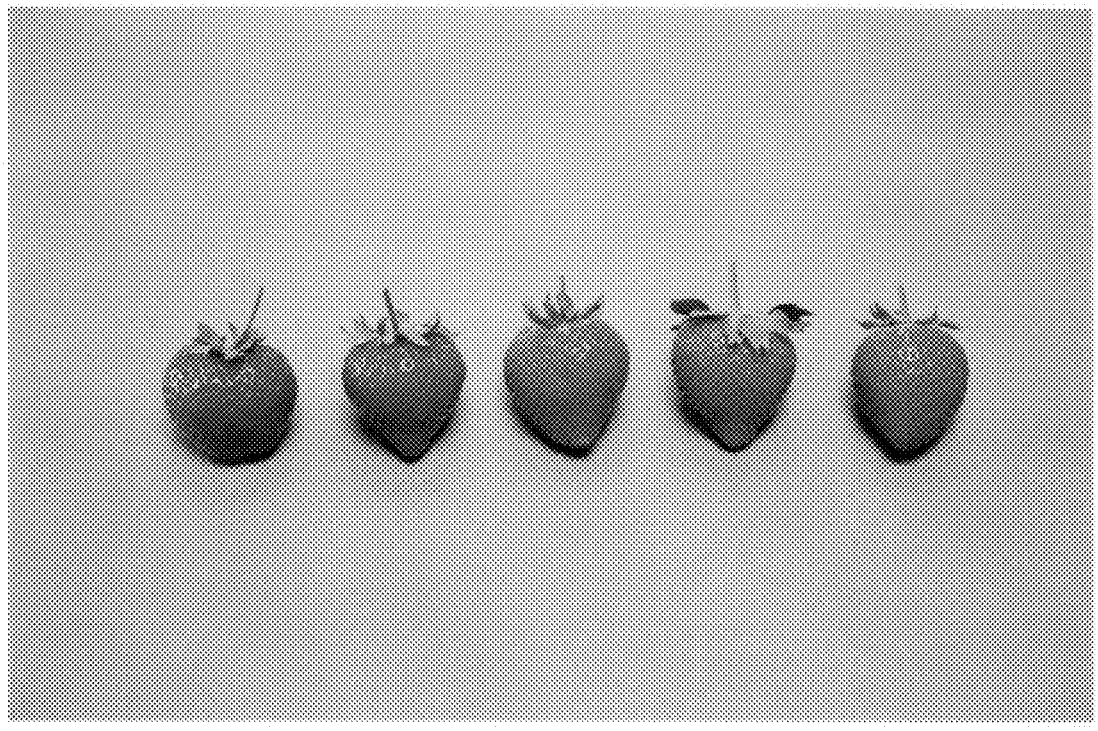
FIG. 4 shows the whole fruit.
Figure 5:
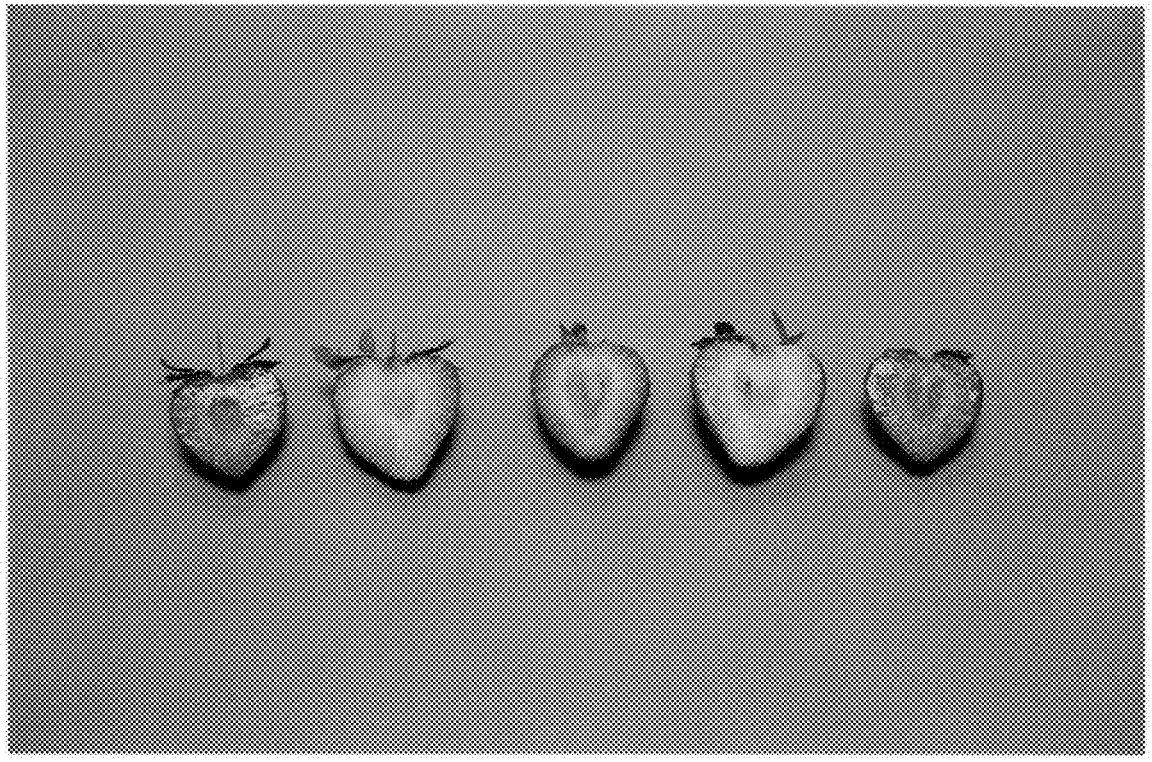
FIG. 5 shows the fruit in longitudinal cross-section.

The following description of 'DrisStrawFifteen' is based on observations taken in Monterey County, Calif. from 2004 to 2009. This description is in accordance with UPOV terminology. Color designations, color descriptions, and other phenotypical descriptions may deviate from the stated values and descriptions depending upon variation in environmental, seasonal, climatic, and cultural conditions. 'DrisStrawFifteen' has not been observed under all possible environmental conditions. The botanical description of 'DrisStrawFifteen' was taken from 9½-month-old plants and the botanical descriptions of the comparison varieties, 'Driscoll Lanai' (U.S. Plant Pat. No. 15,145) and 'DrisStrawNine' (U.S. Plant Pat. No. 20,733), were taken from 10-month-old plants and from 9-month-old plants, respectively. Color terminology follows The Royal Horticultural Society Colour Chart, London (R.H.S.) (2001).

DETAILED BOTANICAL DESCRIPTION

Table 1 shows plant characteristics of the new variety compared with plant characteristics of the commercial varieties 'Driscoll Lanai' and 'DrisStrawNine'. Plant characteristics include plant height, diameter, number of crowns per plant, habit, the density of individual plants and the vigor.

TABLE 1

| Characteristic | 'DrisStrawFifteen' | 'Driscoll Lanai' | 'DrisStrawNine' |
|---|---|---|---|
| Plant height (cm) | 20.5 | 21.9 | 20.9 |
| Plant diameter (cm) | 37.1 | 47.6 | 32.9 |
| Number of crowns/plant | 2 | 5.3 | 3 |
| Habit | Flat globose | Flat | Upright |
| Density of individual plant | Open | Open | Medium |
| Vigor | Medium | Medium | Weak |

Table 2 shows leaf characteristics of the new cultivar compared with leaf characteristics of 'Driscoll Lanai' and 'DrisStrawNine'. Leaf characteristics include terminal leaflet length and width in centimeters, length to width ratio, number of teeth per terminal leaflet, shape of teeth, color of upper side and underside of leaf, leaf shape in cross section, leaf blistering, leaf glossiness, number of leaflets, terminal leaflet margin, terminal leaflet length to width ratio, overall leaf shape and shape of leaf apex and base.

TABLE 2

| Leaf Characteristic | 'DrisStrawFifteen' | 'Driscoll Lanai' | 'DrisStrawNine' |
|---|---|---|---|
| Terminal leaflet length (cm) | 0.7 | 8.1 | 6.8 |
| Terminal leaflet width (cm) | 0.66 | 7.6 | 7.2 |
| Terminal leaflet length/width ratio | 1.1 | 1.07 | 1.0 |
| No. teeth/ terminal leaflet | 19 | 23.4 | 24 |
| Shape of teeth | Rounded | Rounded | Rounded |
| Color of upper surface of leaf | RHS 136A (Dark green) | RHS 139A (Medium green) | RHS 147A (Dark yellow-green) |
| Color of lower surface of leaf | RHS 147B (Medium yellow-green) | RHS 138B (Light green) | RHS 147B (Medium yellow-green) |
| Leaf shape in cross section | Slightly concave | Slightly concave to flat | Concave |
| Leaf blistering | Medium | Medium | Medium |
| Leaf glossiness | Medium | Weak | Between medium and strong |
| No. leaflets | 3 only | 3 only | 3 only |
| Terminal leaflet margin | Revolute to flat | Revolute to flat | Flat |
| Terminal leaflet length/width ratio | As long as broad | | As long as broad |
| Terminal leaflet shape | Orbicular | | Orbicular |
| Terminal leaflet base shape | Rounded | Rounded | Rounded |
| Terminal leaflet apex shape | Rounded | | Rounded |

Table 3 shows information about the petiole, the petiolule, the bract, and the stipule of the new cultivar compared to 'Driscoll Lanai' and 'DrisStrawNine'. This includes petiole length in centimeters, petiole diameter in centimeters, petiole pubescence, pose of hairs on the petiole, color of the petiole, color of the petiolule, petiolule length in centimeters, petiolule diameter in centimeters, bract frequency per petiole, stipule length in centimeters, stipule width in centimeters, stipule pubescence and stipule anthocyanin coloration.

TABLE 3

| Characteristic | 'DrisStrawFifteen' | 'Driscoll Lanai' | 'DrisStrawNine' |
|---|---|---|---|
| Petiole length (cm) | 15.4 | 18.7 | 11.2 |
| Petiole diameter (cm) | 0.279 | | 0.323 |
| Petiole pubescence | Medium | Medium | Dense |
| Petiole pose of hairs | Outwards | Downward | Upwards |
| Petiole color | RHS 145A (Medium yellow-green) | RHS 145A (Yellow-green) | RHS 145A (Medium yellow-green) |
| Petiolule color | RHS 145A (Medium yellow-green) | RHS 145A (Yellow-green) | RHS 145B (Medium yellow-green) |
| Petiolule length (cm) | 0.616 | 1.55 | 0.826 |
| Petiolule diameter (cm) | 0.143 | 0.32 | 0.158 |
| Stipule length (cm) | 3.1 | 3.7 | 3.4 |
| Stipule width (cm) | 0.891 | 1.2 | 0.823 |
| Stipule pubescence | Medium | Medium to dense | Medium |
| Stipule anthocyanin coloration | RHS 145D (Light yellow-green) | | Absent to very weak |

Table 4 shows stolon characteristics of the new cultivar compared to 'Driscoll Lanai' and 'DrisStrawNine'. These characteristics include the number of stolons, average number of daughter plants, the anthocyanin coloration of the stolons, the thickness of the stolons, and the pubescence of the stolons.

TABLE 4

| Characteristic | 'DrisStrawFifteen' | 'Driscoll Lanai' | 'DrisStrawNine' |
|---|---|---|---|
| Stolon number | Many | Many | Medium |
| Average number of daughter plants | 40 | 67 | 35 |
| Stolon anthocyanin | RHS 59B (Dark red-purple) | RHS 60A (Dark red-purple) | Medium |
| Stolon thickness | Medium | Medium to thick | Medium |
| Stolon pubescence | Dense | Dense | Sparse |

Table 5 shows inflorescence characteristics of the new cultivar compared to 'Driscoll Lanai' and 'DrisStrawNine'. These characteristics include inflorescence position relative to foliage, time of flowering, relative flower size, flower diameter in centimeters (measured from petal tip to petal tip), petal shape, relative spacing of petals, petal apex, base and margin, petal length in centimeters, petal width in centimeters, petal length to width ratio, number of petals, petal color, calyx diameter in centimeters (measured on back of flower from sepal tip to sepal tip), diameter of calyx relative to corolla, diameter of inner calyx relative to outer, sepal shape, apex and margin, sepal length in centimeters (measured from sepal tip to point of attachment to receptacle), sepal width in centimeters, number of sepals, receptacle color and anther color.

TABLE 5

| Characteristic | 'DrisStrawFifteen' | 'Driscoll Lanai' | 'DrisStrawNine' |
|---|---|---|---|
| Inflorescence position relative to foliage | Beneath | Level to above | Above |
| Time of flowering (50% of plants at first flower) | Between early and medium | | |
| Flower size | Medium | | Medium |
| Flower diameter (cm) | 2.399 | 2.58 | 2.920 |
| Petal shape | Orbicular | | Orbicular |
| Petal spacing | Overlapping | Overlapping | Overlapping |
| Petal apex shape | Rounded | | Rounded |
| Petal margin | Entire | | Entire |
| Petal base shape | Rounded | | Concave-convex |
| Petal length (cm) | 1.310 | 1.21 | 1.257 |
| Petal width (cm) | 1.269 | 1.29 | 1.332 |
| Petal length/ width ratio | As long as broad | As long as broad | As long as broad |
| Petal length/ width ratio | 1.0 | 0.94 | 0.9 |
| Typical and observed petal number | 6 | | 7 |

TABLE 5-continued

| Characteristic | 'DrisStrawFifteen' | 'Driscoll Lanai' | 'DrisStrawNine' |
|---|---|---|---|
| Petal color (both surfaces) | RHS 155B (White) | RHS 155C (White) | RHS 155B (White) |
| Calyx diameter (cm) | 3.036 | 3.25 | 3.573 |
| Calyx diameter relative to corolla | Larger | Same size to larger | Larger |
| Inner calyx diameter relative to outer | Same size | Larger | Same size |
| Sepal shape | Oval | | Elliptical |
| Sepal apex shape | Convex | | Convex |
| Sepal margin | Entire | | Entire |
| Sepal length (cm) | 1.176 | 1.480 | 1.318 |
| Sepal width (cm) | 0.673 | 0.767 | 0.647 |
| Typical and observed sepal number | 13 | | 14 |
| Receptacle color | RHS 2A (Medium yellow) | | RHS 2B (Medium yellow) |
| Anther color | RHS 174A (Dark greyed-orange) | | RHS 22A (Medium yellow-orange) |

Table 6 shows fruit characteristics of the new cultivar compared to 'Driscoll Lanai' and 'DrisStrawNine'. These characteristics include fruiting truss length in centimeters, fruiting truss diameter, number of berries per truss, fruiting truss attitude, fruiting truss color, fruit length in centimeters, fruit truss width in centimeters, fruit length to width ratio, fruit hollow length and width in centimeters, fruit hollow length to width ratio, fruit weight in grams, relative fruit size, predominant fruit shape, difference in shape between primary and secondary fruits, band without achenes, unevenness of fruit surface, fruit skin color, evenness of fruit color, fruit glossiness, insertion of achenes, achene coloration (sunward and shaded sides of berry) and the number of achenes per berry.

TABLE 6

| Characteristic | 'DrisStrawFifteen' | 'Driscoll Lanai' | 'DrisStrawNine' |
|---|---|---|---|
| Fruiting truss length (cm) | 19.4 | 30.0 | 16.9 |
| Fruiting truss length (general) | Between medium and long | | |
| Fruiting truss diameter (cm) at base of truss | 0.361 | | 0.512 |
| Number of berries per fruiting truss | 5 | | 4 |
| Fruiting truss attitude | Prostrate | Prostrate | Semi-erect |
| Fruiting truss color at base of truss | RHS N144C (Medium yellow-green) | | RHS 144A (Medium yellow-green) |
| Fruit length (cm) | 3.666 | 4.5 | 4.274 |
| Fruit width (cm) | 3.492 | 3.8 | 4.222 |
| Fruit length/width ratio | 1.0 | 1.19 | 1.0 |
| Fruit hollow length (cm) | 1.017 | | 1.341 |
| Fruit hollow width (cm) | 0.442 | | 1.023 |
| Fruit hollow length/width ratio | 2.3 | | 1.3 |

TABLE 6-continued

| Characteristic | 'DrisStrawFifteen' | 'Driscoll Lanai' | 'DrisStrawNine' |
|---|---|---|---|
| Fruit weight (g) | 21.6 | 23.3 | 23.1 |
| Fruit ratio of length/maximum width | As long as broad | | As long as broad |
| Relative fruit size | Medium | | Medium |
| Predominant fruit shape | Conical | Conical to ovoid | Conical |
| Difference in shape between primary and secondary fruits | Between slight and moderate | Slight | Slight |
| Band without achenes | Narrow | Narrow to medium | Narrow |
| Unevenness of fruit surface | Weak | Weak | Weak |
| Fruit skin color | RHS 46A (Dark red) | RHS 45B (Orange red) | RHS 46A (Dark red) |
| Evenness of fruit color | Even | Even | Even |
| Fruit glossiness | Medium | Strong | Medium |
| Insertion of achenes | Below surface | Level with surface | Level with surface |
| Achene coloration (sunward side of berry) | RHS 175A (Dark greyed-orange) | RHS 185B to RHS 154B (Gray purple to yellow-green) | RHS 184A (Dark greyed-purple) |
| Achene coloration (shaded side of berry) | RHS N144A (Medium yellow-green) | RHS 185B to RHS 154B (Gray purple to yellow-green) | RHS 153B (Medium yellow-green) |
| Achenes per berry | 324.0 | 300 | 320 |

Table 7 shows fruit characteristics of the new cultivar compared to 'Driscoll Lanai' and 'DrisStrawNine'. These characteristics include the harvest maturity, insertion of calyx, pose of calyx segments, size of calyx in relation to fruit, adherence of calyx, firmness of flesh, color of the fruit flesh, evenness of the flesh color, distribution of flesh color, hollow center, sweetness of fruit, acidity of fruit, texture of fruit when tasted, type of bearing, grams of fruit per plant.

TABLE 7

| Characteristic | 'DrisStrawFifteen' | 'Driscoll Lanai' | 'DrisStrawNine' |
|---|---|---|---|
| Harvest interval | Late March to early November | Late March to early November | Late March to early November |
| Harvest maturity | Between early and mid-season | | |
| Insertion of calyx | Set above fruit | Level | Level |
| Pose of calyx segments | Spreading | Spreading to reflexed | Spreading |
| Size of calyx in relation to fruit | Smaller and larger | Smaller | Larger |
| Adherence of calyx | Strong | Strong | Strong |
| Firmness of flesh | Firm | Medium | Medium |
| Color of the flesh | RHS N155B (White) and RHS 46B (Dark red) | RHS 47C (Orange-red) | RHS 155C (White) and RHS 41A (Medium red) |
| Evenness of flesh color | Slightly uneven | Uneven | Uneven |
| Distribution of flesh color | Marginal and central | Marginal and central | Marginal and central |
| Hollow center | Small | Medium | Small |
| Sweetness | Strong | Medium | Medium |
| Acidity | Medium | Medium | Medium |
| Texture when tasted | Medium | Fine | Medium |
| Type of bearing | Fully everbearing | Partially everbearing | Fully everbearing |

TABLE 7-continued

| Characteristic | 'DrisStrawFifteen' | 'Driscoll Lanai' | 'DrisStrawNine' |
|---|---|---|---|
| Grams of fruit/plant | 1,513 | 1,679 | 1,505 |

Table 8 shows pest, stress and disease characteristics of the new cultivar compared to 'Driscoll Lanai' and 'DrisStrawNine'.

TABLE 8

| Pest, Stress, or Disease | 'DrisStrawFifteen' | 'Driscoll Lanai' | 'DrisStrawNine' |
|---|---|---|---|
| *Tetranychus urticae* | Moderately susceptible | Susceptible | Moderately susceptible |
| *Botrytis* fruit rot | Moderately susceptible | Susceptible | Susceptible |
| Powdery mildew | Moderately susceptible | Susceptible | Between moderately susceptible and susceptible |
| *Verticillium* wilt | Moderately resistant | Moderately resistant | Susceptible |
| Rain | Between moderately resistant and moderately susceptible | | |

COMPARISON WITH PARENTAL AND COMMERCIAL CULTIVARS

When 'DrisStrawFifteen' is compared to the proprietary female parent 'Driscoll Lanai' (U.S. Plant Pat. No. 15,145), 'DrisStrawFifteen' is fully everbearing while 'Driscoll Lanai' is partially everbearing. In addition, 'DrisStrawFifteen' has a strong sweetness of fruit while 'Driscoll Lanai' has a medium sweetness of fruit. Finally, 'DrisStrawFifteen' has smaller fruit size (length: 3.666 cm; width: 3.492 cm) than 'Driscoll Lanai' (length: 4.5 cm; width: 3.8 cm).

When 'DrisStrawFifteen' is compared to the proprietary male parent '38J181' (unpatented), 'DrisStrawFifteen' has larger fruit and is more prone to bruising during handling than '38J181'.

When 'DrisStrawFifteen' is compared to the commercial variety 'DrisStrawNine', the petiole pose of hairs for 'DrisStrawFifteen' is outwards while the petiole pose of hairs for 'DrisStrawNine' is downward. In addition, 'DrisStrawFifteen' is moderately resistant to *Verticillium* wilt while 'DrisStrawNine' is susceptible to *Verticillium* wilt.

We claim:

1. A new and distinct cultivar of strawberry plant as described and shown herein.

* * * * *